(12) United States Patent
Tajima et al.

(10) Patent No.: US 7,071,006 B2
(45) Date of Patent: Jul. 4, 2006

(54) CARRIER HOLDING MICRO-SUBSTANCES, SYSTEM SUSPENDING SUCH CARRIERS APPARATUS FOR MANIPULATING SUCH CARRIERS AND METHOD OF CONTROLLING POSITIONS OF SUCH CARRIERS

(75) Inventors: Hideji Tajima, Inagi (JP); Yoshiro Okami, Ota-ku (JP)

(73) Assignee: Precision System Science Co., Ltd., Inagi (JP)

( * ) Notice: Subject to any disclaimer, the term of this patent is extended or adjusted under 35 U.S.C. 154(b) by 256 days.

(21) Appl. No.: 10/042,373

(22) Filed: Dec. 27, 2001

(65) Prior Publication Data
US 2002/0064866 A1 May 30, 2002

Related U.S. Application Data

(62) Division of application No. 09/202,229, filed as application No. PCT/JP97/01962 on Sep. 9, 1997, now abandoned.

(30) Foreign Application Priority Data

Jun. 10, 1996 (JP) .................................. 8-147574

(51) Int. Cl.
*G01N 33/553* (2006.01)

(52) U.S. Cl. .............. 436/526; 436/518; 436/512; 436/531; 436/548; 436/800; 436/808; 436/819; 436/822; 436/828; 427/550; 427/127; 427/414; 427/560; 427/598; 427/601; 428/402; 435/4; 435/7.2; 435/7.4; 435/7.7; 435/7.8

(58) Field of Classification Search ................ 436/526, 436/518, 512, 531, 548, 800, 808, 819, 822, 436/828; 427/550, 127, 414, 560, 598, 601; 428/402; 435/4, 7.2, 7.4, 7.7, 7.8
See application file for complete search history.

(56) References Cited

U.S. PATENT DOCUMENTS 3,985,649 A * 10/1976 Eddelman .................... 210/695

(Continued)

FOREIGN PATENT DOCUMENTS

JP 62-112063 A 5/1987

(Continued)

*Primary Examiner*—Long V. Le
*Assistant Examiner*—Pensee T. Do
(74) *Attorney, Agent, or Firm*—Haynes and Boone, LLP (57) ABSTRACT

Carriers hold remote-acting bodies which can be manipulated by a remote force, and also hold a micro-substance which is a target substance of an assay. The remote-acting bodies are manipulated in order to control the positions of the micro-substances, so as to execute assays for various target substances efficiently, at low cost, easily, and reliably. Various aspects of interest include the carriers which hold the micro-substances, a system suspending the carriers, an apparatus for manipulating the carriers, and a method of controlling the position of the carriers.

8 Claims, 4 Drawing Sheets

U.S. PATENT DOCUMENTS

| | | | |
|---|---|---|---|
| 4,115,535 A | | 9/1978 | Giaever |
| 4,659,678 A | * | 4/1987 | Forrest et al. ............... 436/512 |
| 4,935,147 A | * | 6/1990 | Ullman et al. ............... 210/695 |
| 5,464,001 A | * | 11/1995 | Peck .......................... 124/25.6 |
| 5,508,164 A | * | 4/1996 | Kausch et al. ................. 435/6 |
| 5,541,072 A | * | 7/1996 | Wang et al. ................ 435/7.21 |
| 5,646,001 A | | 7/1997 | Terstappen et al. |
| 5,698,271 A | * | 12/1997 | Liberti et al. ............... 427/550 |
| 5,736,033 A | * | 4/1998 | Coleman et al. ............ 210/122 |
| 5,770,388 A | * | 6/1998 | Vorpahl .................... 435/7.25 |

FOREIGN PATENT DOCUMENTS

| | | |
|---|---|---|
| JP | 62-171677 A | 7/1987 |
| JP | 62-502990 A | 11/1987 |
| JP | 1-227061 A | 9/1989 |
| JP | 1-265972 A | 10/1989 |
| JP | 5-64596 A | 3/1993 |
| JP | 7-8292 A | 1/1995 |
| JP | 8-52378 A | 2/1996 |
| JP | 8-94619 A | 4/1996 |

* cited by examiner

CARRIER HOLDING MICRO-SUBSTANCES, SYSTEM SUSPENDING SUCH CARRIERS APPARATUS FOR MANIPULATING SUCH CARRIERS AND METHOD OF CONTROLLING POSITIONS OF SUCH CARRIERS

This application is a divisional of U.S. Ser. No. 09/202,229, filed Jul. 26, 1999 now abandoned, which is a 371 of International Application No. PCT/JP97/01962, filed Jun. 9, 1997, which claims priority to Japanese Patent Application No. 8-147574, filed Jun. 10, 1996.

FIELD OF THE INVENTION

This invention relates to a carrier holding micro-substances, system suspending such carriers, apparatus for manipulating such carriers and method of controlling positions of such carriers, which is used for the work of measuring, separating, pipetting, clarifying, concentrating, diluting, observing, extracting, recovering, isolating and so on by transferring or capturing micro-substances suspended in a liquid, gas or solid, for examples, which are useful substances such as medical supplies, gene substances such as DNA etc. and immune substances such as antibody.

BACKGROUND OF THE INVENTION

So far, in such various fields as medical treatment, medicine, chemistry, physiological hygiene, sanitary, biology, food, or material and so on, it is necessary for control of a position in order to separate a target substance of assays etc. and capture the pure target substance.

For example, in the field of the medical treatment, there are such various methods of assay as chemiluminescence methods (CL method) such as an enzyme immunoassay (EIA) that utilizes an antigen-antibody reaction, a chemiluminesence immunoassay (CLIA) in a narrow sense in which a chemical illuminescent compound is used for marking as a tracer for immunoassay, and a chemilluminescent enzyme immunoassay (CLEIA) which detects enzyme activity with high sensitivity by using a chemical luminescent compound in a detection system.

As an inspection method, using any of the techniques as described above, there have been known the magnetic particles method using magnetic particles each having a surface coated with an antigen or an antibody, the latex method using latex having a surface coated with an antigen or an antibody, the beads method using spherical beads (non-magnetic) each having a surface coated with an antigen or an antibody, or the so-called tubecoating method using cells each having an inner wall coated with an antigen or an antibody. When taking into account efficiency of capturing an antigen or an antibody as well as production cost and running cost, however, methods using magnetic bodies such as magnetic particles or beads are far more advantageous.

Incidentally, when the magnetic particles per se hold micro-substances, the less the size of each magnetic particle is formed, the more the quantity of the micro-substances can be captured by whole the magnetic particles, on the condition that the total mass or volume of whole the magnetic particles is fixed. Because, reduced size of magnetic particle results in increase in the ratio of surface to volume. As a magnetic charge per a magnetic particle is reduced and an influence of the magnetic field on each magnetic particle is reduced certainly in this case, however, there has been a problem that an attraction becomes weaker and the control of magnetic field becomes more difficult.

On the other hand, if a volume of each magnetic particle increases, the influence of the magnetic field to each magnetic particle enhances, the attraction becomes stronger, and a control of magnetic field becomes easier. On the condition that the total mass of the magnetic particles is equal, however, there has been a problem that the magnetic particle is hard to capture micro-substances and the efficiency in capturing micro-substances decreases.

Furthermore, capturing substances on magnetic particles per se requires such treating as coating and so on. Particularly, there has been a problem that to treat the surface of magnetic particle per se optionally so as to enhance the efficiency in capturing micro-substance is technically and costly difficult.

It is a first object of the present invention to provide an improved carrier holding micro-substances, system suspending such carriers, apparatus for manipulating such carriers and method of controlling positions of such carriers, therefore.

It is a second object of the present invention to provide a general-purpose carrier holding micro-substances, system suspending such carriers, apparatus for manipulating such carriers and method of controlling positions of such carriers which can hold various substances that can not directly affected by remote forces, and that can not directly be bonded to magnetic particles, and can hold various remote-acting bodies, so that diverse inspections and so on can be executed for various target substances.

It is a third object of the present invention to provide a carrier holding micro-substances, system suspending such carriers, apparatus for manipulating such carriers and method of controlling positions of such carriers which combines a low-cost carrier which is superior in capturing target substances and is easily treated but has not a remote operating character, with remote-acting bodies which are superior in remote operating and controlling, without necessity of depending upon magnetic particles having an extraordinary particular surface or substance for capturing target substances, and, which needs not treat the magnetic particles per se, is produced at low cost, is easy to operate remotely, has a super capturing-ability, can efficiently and promptly process with high precision in determining quantity, and is easy to be dealt with.

It is a forth object to provide a carrier holding micro-substance, system suspending such carriers, apparatus for manipulating such carriers and method of controlling positions of such carriers which can execute various actions and precision and complex controls by reliable remote operating.

It is a fifth object to provide a carrier holding micro-substances, system suspending such carriers, apparatus for manipulating such carriers and method of controlling the positions of such carriers which is chemically stable, has not bad-influence upon target substances of inspections for living things, and is reliable.

It is a sixth object to provide a carrier holding micro-substances, system suspending such carriers, apparatus for manipulating such carriers and method of controlling positions of such carriers which can easily separate a target substance from the remote-acting bodies such as magnetic particles, collect and recover only the pure target substance, and change concentration.

It is a seventh object to provide a carrier holding micro-substances, system suspending such carriers, apparatus for manipulating such carriers and method of controlling positions of such carriers which can treat plural suspension systems without mixing these systems, can establish a uniform state, and can transfer and carry the useful substances (such as antibiotic and so on) to destination without contamination.

It is an eighth object to provide a carrier holding micro-substances, system suspending such carriers, apparatus for manipulating such carriers and method of controlling positions of such carriers which can effectively be available to easy and rapid process of test-analysis for useful substances, extraction-analysis for gene substances (DNA and so on), and detection-analysis for immune substances, and, can contribute to automatizing a clinical test.

It is a ninth object to provide a carrier holding micro-substances, system suspending such carriers, apparatus for manipulating such carriers and method of controlling positions of such carriers which can prevent from clog and so on and improve the efficiency of filtration and absorption by using the carriers as auxiliary chemicals of filter and absorption, controlling the density of carriers with disposition and direction of magnetic field.

It is a tenth object to provide a carrier holding micro-substances, system suspending such carriers, apparatus for manipulating such carriers and method of controlling positions of such carriers which can safely, easily, and automatically transfer a target substance between reaction vessels in order, in the case of a multistage chemical reaction.

It is an eleventh object to provide a carrier holding micro-substances, system suspending such carriers, apparatus for manipulating such carriers and method of controlling positions of such carriers which can easily, rapidly, and automatically inspect the efficient concentration of antibiotic by easy and rapid test with absorbing the biological active substance (such as antibiotic) or test bacterium (such as antibiotic test bacterium: a colon bacillus) to the carriers, or cultivating them in the carriers.

It is an twelfth object to provide a carrier holding micro-substances, system suspending such carriers, apparatus for manipulating such carriers and method of controlling positions of such carriers which can cultivate, recover, concentrate, or analyze substances (such as iron filings, dust, environmental pollution, food pollution, addition), microorganisms or cells of plants and animals.

SUMMARY OF THE INVENTION

According to a first aspect of the invention, the above mentioned objects are achieved by providing a carrier holding micro-substances comprises a carrier holding one or more remote-acting bodies capable of being manipulated for positions thereof by a remote force, and one or more micro-substances containing a target substance of an assay and so on in the surfaces of the carrier, wherein positions of micro-substances are controlled by a remote manipulation of the remote-acting bodies which are held together with micro-substances in the surfaces of the carrier.

Here, the micro-substances include a target substance for an assay, a test, multiplication, or extraction and so on. The micro-substances are not limited to the target substance, but can include other substances such as marker substances or intervene substances and so on.

The target substance, the intervene substance or the other substance is not always limited to a single kind. A size of the micro-substance is not always limited to a fixed one. But, for example, it may be about 0.1 µm to 1 mm. Furthermore, the micro-substances include living bodies, namely, such microorganisms as bacteria, or viruses.

The "remote-acting body" is the one whose position can be manipulated by such remote force generated by a magnetic field, an electronic field, light, temperature gradient, and pressure gradient, sonic wave and so on. For example, as the remote-acting bodies, magnetic particles are used for the magnetic field, charge particles or dielectric substances are used for the electric field, particles having an air bubble or an endothermic element capable of rising by a buoyant force generated in volume heated and expanded by ray or heat are used for light or temperature field, or moving bodies by vibration with applying super sonic wave or pressure wave, are used. The remote-acting body is not always manipulated by a single kind of force. Such a remote-acting body as a charged magnetic substance can be manipulated by various kinds of remote forces. Micro-organisms may be used as the remote-acting bodies.

The "carrier" is capable of holding remote-acting bodies and micro-substances in the surfaces thereof. They are held by fixing, adsorption, adhesion, or reaction with a reaction substance coated thereon.

The size of the remote-acting body or the carrier is not necessarily fixed. It is the same orders as the micro-substance, for example, about 0.1 µm (100 nm) to about 1000 µm($10^6$ nm=1 mm).

"Control of position" includes in addition to control of transferring, control of collecting, oscillating, rotating, capturing, speed, separating, suspending, or cleaning. The present invention satisfies both superior remote-acting ability and superior capturing ability, by holding a remote-acting body or bodies such as magnetic particles etc. and micro-substances in the carrier. Hence, the present invention can enhance efficiency of assay and so on, and can quickly execute a processing with high precision in deciding quantity, at low cost, without trouble. Various movements, and precision and complex controls are executed by remote-acting operation of the present invention. The present invention provides the carrier holding micro-substances, which can transfer and carry such useful substances as medical supplies (immune substance and so on) to the destination, without contamination.

According to a second aspect of the invention, the above mentioned objects are achieved by providing a carrier holding micro-substances, wherein the carrier holds the remote-acting bodies and micro-substances by fixing a plurality of holes, cavities, concavities or convexities, adsorption or adhesion in the surface per se, reaction by a prescribed reaction substance coated thereon, or combination therewith.

Here, "holes, cavities" include in addition to dips-like in surfaces, the ones penetrating the carrier such as porous cavities which include the one such as fiber or gel. Also, "holes, cavities, concavities or convexities", coating and so on may be not always formed in the carriers. Fixing, adsorption, adhesion, or, reaction may be done not only in the surfaces or the carrier, but also in the surfaces of the micro-substance or remote-acting substance. For instance, the carrier may be held in holes formed in a bigger remote-acting body, and the micro-substances are held in the carrier further.

"Fixing" means to hold mainly by a mechanical force such as a friction. For example, it includes the meaning to hold by inserting or slipping into holes and so on. To be able to capture micro-substances and so on by fixing, an affinity between the carrier and micro-substances and so on in fixing is necessary. The affinity can mainly be determined by the size of micro-substance, remote-acting ability, size of remote-acting bodies, or size of holes, cavities, concavities or convexities.

"Adsorption" means the phenomena that substances in gas phase or liquid phase reach to an equilibrium at different concentration from that of the inside phase, on the surface between one phase and the other contacting phase. The word, adsorption includes physical adsorption and chemical adsorption. Here, it is used in such a broad meaning as adsorption by various reactions or electromagnetic forces. Further, adsorption by reaction or electromagnetic force includes various modes such as absorption by electrostatic force (Coulomn force), magnetic force or intermolecular force as van der Waals' force, hydrogen bond, ionic bond, or covalent bond.

"Reaction" includes agglutination (reaction of solidification). Reaction can bond only solidified target substance and can remind non-solidified substances in liquid without bonding. "Adhesion" means to hold by using an adhesive power of adhesives and so on. "Reaction by a prescribed reaction substance coated thereon" includes, for example, antigen-antibody reaction. In this case, a target substance is an antigen that is captured by this reaction, and the carrier is coated by an antibody reacting with the antigen.

In the case that DNA substance is a target substance, the DNA substance can be captured with the reaction of hydrogen bond, by the carrier coated by basic ingredients (adenin←→thymine, guanine←→cytosine) which is complementary to the basic ingredients of the DNA. Coating may be formed on micro-substances or remote-acting bodies, instead of the carrier. Furthermore, whole the surfaces are not always covered with coating. It follows from "combination therewith" that fixing and absorption can exist together and that the absorption can be done on the surfaces of micro-substances fixed to the carrier, for instance.

Figure 1:
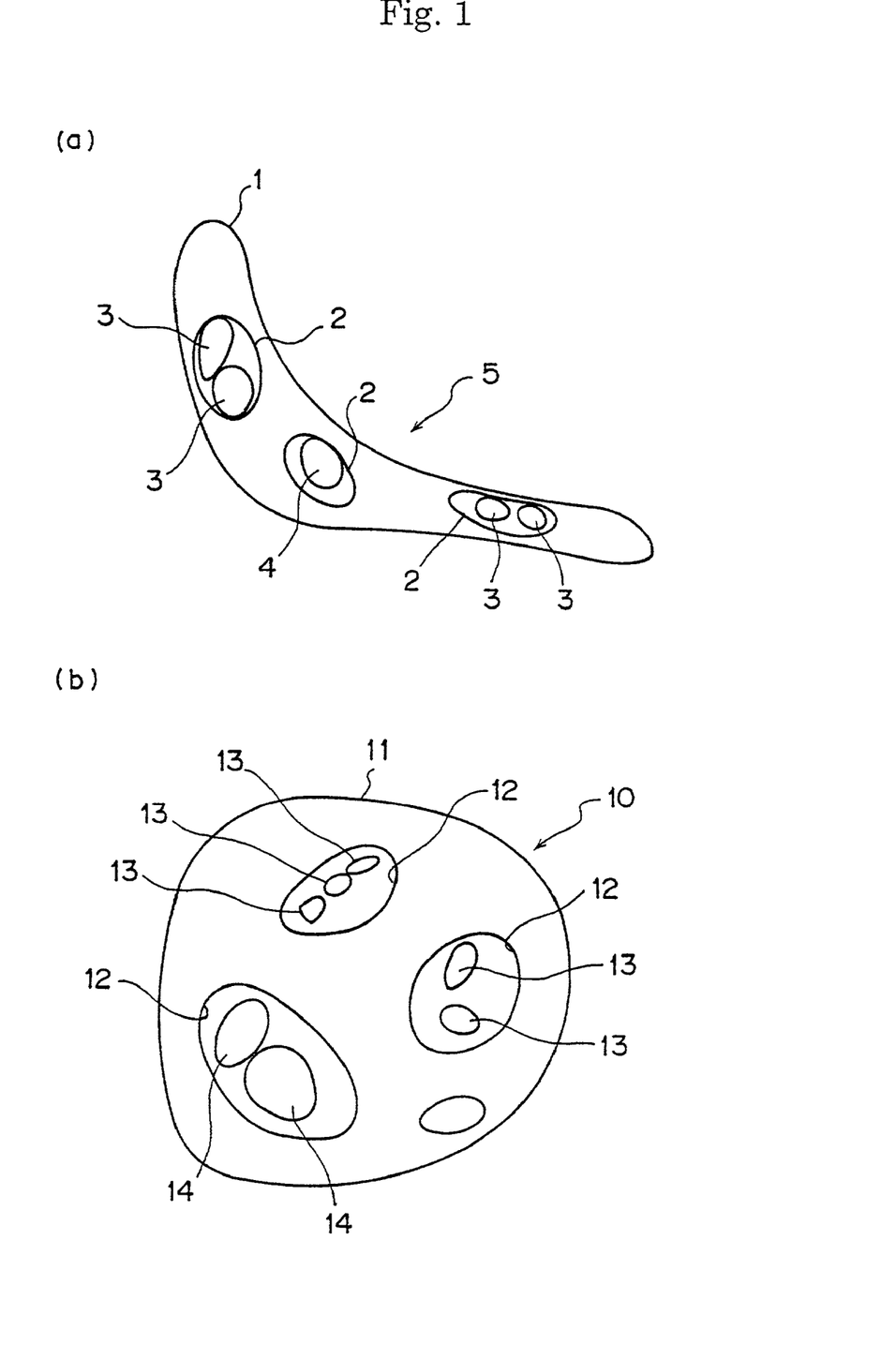
FIG. 1 is an enlarged schematic illustration of the carrier holding micro-substances of the first embodiment of the invention.

In FIG. 1 (a) (b), enlarged micro-substances-holding-carriers are imitatively exemplified, which are of various shapes or of indefinite shapes and are held by remote-acting bodies and micro-substances. FIG. 1 (a) shows a micro-substances-holding-carrier 5, which holds remote-acting bodies 3 and micro-substances 4 in a plurality of holes 2 of the fibrous carrier 1. FIG. 1 (b) shows a micro-substances-holding-carrier 10, which holds remote-acting bodies 13 and micro-substances 14 in a plurality of holes 12 of the spherical carrier 11. The shape of the carrier may include torus and so on, in addition to these shown shapes. Thus, as remote-acting body and micro-substance can be held in the carrier in various way, inspections for various substances can be executed.

According to a third aspect of the invention, the above mentioned objects are achieved by providing a carrier holding micro-substances, wherein the carrier is formed by organic substances such as high molecular compounds, inorganic substances such as ceramics or metals or, living bodies.

Here, "high molecular compounds" include fibrous substances and synthetic resins. The present invention is capable of executing various controls or inspections and so on, because various carriers can be selected according to the purpose of inspections etc. or used kinds of substances.

According to a fourth aspect of the invention, the above mentioned objects are achieved by providing a carrier holding micro-substances, wherein the carrier is made of fibrous substance such as cellulose.

Here, "fibrous substance" includes a synthetic fibrous such as nylon etc. in addition to the cellulose. As the surfaces of fibrous substance such as cellulose have a plurality of cavities, concavities, convexities or holes, the surfaces can capture various substances. The present invention has not only above-mentioned effect, but also the effect that is capable of using for various purposes. Because the fibrous substance such as cellulose and so on is chemically stable, and can be used for suspension of various substances. Also, the fibrous substance is easy to be treated, and can be treated at low cost. The fibrous substance is light, and can easily be controlled. Cellulose may be formed to be torus-like or fibrous-like as well as spherical-like.

Furthermore, since the surfaces of fibrous substance such as cellulose etc. have holes or cavities and so on, fibrous substance needs not be treated by coating of predetermined substance etc. on the carrier, so as to capture target substances. Fibrous substances can easily capture these substances by agitating or suspending with the remote-acting bodies and micro-substances, can easily construct the carriers holding micro-substances, and can satisfy both ability of capture and remote-acting ability.

Consequently, the reliable carriers holding micro-substances are promptly provided at low cost, without requiring much labor. As the fibrous substance like cellulose is easy to be treated, treatment for improving capturing efficiency can easily be done at low cost.

Further, in the present invention, micro-substances can be separated from the carriers once held by remote-acting bodies and micro-substances. For example, when the carrier is cellulose, the carrier can be excluded by dissolving the cellulose with making use of enzyme in a concentration process of micro-substances.

According to a fifth aspect of the invention, the above mentioned objects are achieved by providing a carrier holding micro-substances, wherein micro-substances include one or more kinds of intervene substances through which said target substances or the remote-acting bodies are held in the carrier.

The present invention is capable of holding the substances that can not directly be bonded to the carrier, in the carrier. For example, if the carrier is apt to bond the antigen and is hard to bond the antibody, it is appropriate that the carrier can capture antigen through the antibody held on the carrier. Therefore, the present invention can apply to the various substances.

According to a sixth aspect of the invention, the above mentioned objects are achieved by providing a carrier holding micro-substance, wherein the micro-substances include auxiliary substances such as marker substances and so on.

The present invention facilitates to analyze inspections and so on, and is capable of accelerating or delaying reactions in inspections and executing various processing. "Auxiliary substances" include catalyst substances for accelerating inspections and so on, in addition to said marker substances. Furthermore, the auxiliary substances may indirectly be held in the carrier through target substances and so on, without bonding the carrier directly.

According to a seventh aspect of the invention, the above mentioned objects are achieved by providing a carrier holding micro-substances, wherein the remote-acting bodies are made of magnetic substances. Hence, the present invention can easily execute a reliable and precision control superior in remote-acting operation, at low cost.

Here, "magnetic substance" includes para-magnetic substance or ferro-magnetic substance, which receives a virtue of a magnetic field. The magnetic substances include the one having spherical shape of big diameter or micro-particles like a grain, and the diameter is not necessarily fixed. The shape is not limited to the spherical one. These shapes can be applicable to the case of the charged body, dielectric body or transparent body and so on as mentioned below. Thus, the present invention can faithfully and reliably control positions at low cost, with excellent remote-acting ability.

According to an eighth aspect of the invention, the above mentioned objects are achieved by providing a carrier holding micro-substances, wherein the remote-acting bodies are made of charged bodies or substances having a different dielectricity from that of the surrounding suspended system. “Charged body” means the one having charge. For example, it includes a ferro-dielectric body having a spontaneous dielectric polarization without an electric field. The dielectricity of the remote-acting bodies is different from the suspension system around them and is higher or lower than that of the systems. As the charge body of lower dielectricity has an opposite polarity from the higher one, it moves in opposite direction to the electric field. Consequently, the present invention can execute easy, reliable and precision control of remote-acting operations. Furthermore, the present invention is capable of various and easy controls by combining with various remote-acting bodies.

According to a ninth aspect of the invention, the above mentioned objects are achieved by providing a carrier holding micro-substances, wherein the remote-acting bodies are micro-organisms having such taxis as lumino-taxis or magno-taxis. Here, for example, “magno-taxis micro-organisms” include micro-organisms such as cells or bacteria etc. in which magnetic substances are artificially or naturally contained. When micro-organisms are used, it is necessary that the other substances do not affect a bad influence to the micro-organisms, or, the micro-organisms do not affect the other substances conversely. The present invention can easily use micro-organisms without treating substances, and can have the micro-organisms move complicatedly.

According to a tenth aspect of the invention, the above mentioned objects are achieved by providing a carrier holding micro-substance, wherein the remote-acting bodies are expandable particles whose volume changes in accordance with temperature or pressure. For example, a substance having a high thermal expansion coefficient can easily transfer upward or downward by expansion or contraction according to rising temperature or pressure of whole the suspension system, at low cost. The expandable particles are the one enclosed a gas susceptible to expand and contract compared with the surrounding liquid therein.

According to an eleventh aspect of the invention, the above mentioned objects are achieved by providing a carrier holding micro-substance, wherein the remote-acting bodies are made of transparent substances or opaque substances. The carrier holding the remote-acting particles and so on in one united body can cause to be moved or trapped (laser trap) by irradiating a laser to transparent particles used as remote-action particles, for example, such as polystyrene latex, or silica micro-particles. Or, the carrier in one united body can cause to be moved upwardly or downwardly by irradiating the laser to opaque particles or not, so as to expand or concentrate by heat.

According to a twelfth aspect of the invention, the above mentioned objects are achieved by providing a carrier holding micro-substances, wherein the remote-acting bodies are magnetic particles and the carriers are made of cellulose.

The size of the carrier is determined according to the purpose of the assay etc., the kinds or sizes of a target substance, magnetic particles to be held and suspension systems. As the present invention can provide the carrier holding micro-substances which has both superior remote-acting ability and superior capturing ability, the present invention can efficiently, rapidly and reliably execute inspection at low cost.

According to a thirteenth aspect of the invention, the above mentioned objects are achieved by providing a system suspending carriers holding micro-substances is suspension of remote-acting bodies, micro-substances and the carriers which are described in the first to the twelfth aspects of the invention in a liquid, a gas or a solid. “Solid” includes, for example, such gel-like substance as alginic acid, paste, agaragar-like substance and so on. As the present invention can provide the carrier holding micro-substances which has both superior remote-acting ability and superior capturing ability, the present invention can efficiently, rapidly and reliably execute the assay, at low cost.

Furthermore, in the present invention, the carriers holding micro-substances are capable of various movements and precision and complicated controls by sure remote-acting operation. And the present invention provides the carrier holding micro-substances which can move and carry such useful substances as medical supplies (antibody and so on) to the destination, without contamination.

The present invention can analyze and test the useful substances, and can extract and analyze the gene substance (DNA and so on), and detect the immune substance (antibody etc.) and so on.

According to a fourteenth aspect of the invention, the above mentioned objects are achieved by providing a system suspending carriers holding micro-substances, wherein the carrier is a sterilized cellulose-carrier having a plurality of cavities or holes, the remote-acting bodies are sterilized magnetic particles, micro-substances contain micro-organisms being target of an assay and sterilized reductive enzyme used as a marker substance, and the liquid is a sterilized liquid culture medium.

Here, the size of the cavities or hole is large enough to be able to perform orientation of magnetic particles and be able to control positions of carrier holding micro-substances by magnetic field. For example, diameter of the hole is about 10 μm in the case of the cellulose carrier of about 150 μm. Thus, even if a magnetic particle is small, the positions of carrier can be controlled as long as holes with size being large enough to perform orientation to accept the influence of the magnetic field and bond the magnetic particles. “Cellulose carrier” includes the one made of cellulose or the one such as cellulose acetate made from cellulose.

The present invention provides with the carrier holding micro-substances, which satisfies both remote-acting ability and capturing ability, is chemically stable, does not affect target substances such as living things for assays and so on, is reliable, and is capable of being selected diversely according to target substances. Furthermore, the carrier holding micro-substances can transfer and carry a useful substance such as medical supplies (antibiotic and so on) to the destination without contamination.

The present invention can effectively utilize for easy and rapid processing of inspection and analyze of useful substances, extraction and analyze of gene substance (DNA and so on), and inspection and analyze of immune substance (antibody) and so on, and can contribute to the automatic performance of the clinical inspection and so on.

Furthermore, such substances and cells that can be adsorbed to the carriers can be recovered and concentrated by making use of orientation in magnetic field.

According to a fifteenth aspect of the invention, the above mentioned objects are achieved by providing a system suspending carriers holding micro-substances, wherein the carrier is a cellulose-carrier having a plurality of cavities or holes, the remote-acting bodies are magnetic particles, and micro-substances are antibiotics or anticancer substances.

Here, the size of each substance is various according to kinds of the suspension systems. For example, the carrier is the sphere having a diameter of about 100 μm, the cavities or holes have a dimension of about 10 μm, the magnetic particles are about 1 μm, and the concentration of the carriers in liquid is about 1000 sphere/cc. If kanamycin is used as an immune substance, the concentration of the carriers is about 1000 sphere/cc.

The present invention has not only the above mentioned effects, but also has effects being chemically stable, affecting no bad influence to target substances for inspection etc., being reliable, and enabling to select appropriate substances variously according to target substances and so on.

Furthermore, the carrier holding micro-substances can transfer and carry useful substances such as medical supplies (antibiotic and so on) to the destination, without contamination.

The present invention can effectively utilize for easy and rapid processing of inspection and analyze of useful substances, extraction and analyze of gene substance (DNA and so on), and inspection and analyze of immune substances (antibody) and so on, and can contribute to the automatic performance of the clinical inspection and so on. Furthermore, such substances and cells that can be adsorbed to the carriers, can be recovered and concentrated by making use of orientation in magnetic field.

According to a sixteenth aspect of the invention, the above mentioned objects are achieved by providing a suspension system for carriers holding micro-substances, wherein the remote-acting bodies and the carriers are used as filtering auxiliary chemicals for filtering so that micro-substances being hard to filter can be filtrated.

The present invention makes filtrating separation be more reliable, less contaminated, and less laborious than a filter. The present invention causes micro-substances that are hard to be filtrated, to facilitate to be filtrated surely by suspending the remote-acting bodies and carriers. The present invention can improve the efficiency of adsorbing and filtrating by using the carrier as auxiliary chemicals for adsorbing and filtering, by utilizing orientation by magnetic field, by controlling the density of carriers, and by avoiding clog and so on. Furthermore, the present invention can execute multi-stage chemical reactions by transferring the carriers between containers in order, safely, automatically and easily.

According to a seventeenth aspect of the invention, the above mentioned objects are achieved by providing an apparatus for manipulating carriers holding micro-substances comprises a container accommodating the suspension system or a liquid passage passing the suspension, and remote-manipulating means mounted out of the container or the liquid passage to manipulate the remote-acting bodies in the container or the liquid passage remotely.

Here, "the liquid passage" is the one which a liquid passes through, and "container" is the one which accommodating a liquid. The carrier holding micro-substances combines the remote-acting bodies having superior remote-acting ability with the carriers having superior capturing-ability, can satisfy the characteristics of superior remote-acting ability and superior capturing-ability, and can efficiently and rapidly treat assay and so on, with high precision in quantity.

Furthermore, the present invention enables various movements and precision and complicated controls by sure remote-acting operation. Also, the present invention provides the carriers holding micro-substances that can transfer and carry such useful substances as medical supplies (immune substances and so on) to the destination, without contamination. The present invention can effectively be utilized for easy and rapid processing of inspection and analyze of useful substances, extraction and analyze of gene substance (DNA and so on), and inspection and analyze of immune substances (antibody) and so on.

According to an eighth aspect of the invention, the above mentioned objects are achieved by providing an apparatus for manipulating carriers holding micro-substances, wherein the remote-manipulating means is a magnetic source such as a permanent magnet or a solenoid generating magnetic field to be applied to the remote-acting bodies. The apparatus can faithfully, surely, and efficiently control, and can not only transfer, separate or collect the carrier, but also agitate or clean.

According to a nineteenth aspect of the invention, the above mentioned objects are achieved by providing an apparatus for manipulating carriers holding micro-substances, wherein the remote-manipulating means is one or more electrodes which alternative current or direct current voltage is supplied when the remote-acting bodies are made of charge bodies or dielectric bodies, and is a controllable heat source or a pressure control means when the remote-acting bodies are expandable particles whose volume change, in accordance with temperature or pressure.

In the present invention, the apparatus can not only transfer or collect the carriers, but also can surely and efficiently agitate or clean by driving the remote-manipulating means. "Alternating current voltage" which has a fixed high frequency, prevents from generating electrode reaction (electrolysis).

In the present invention, the apparatus can be used for electrophores from one electrode to another electrode. Here, two electrodes are oppositely arranged so that the container is put between the electrodes, and the one electrode is formed to be sharp. Besides, the direction for movement of carriers in electrophores depends upon whether the dielectricity of the dielectric body is lower or higher than the surrounding liquid or gas.

Furthermore, the present invention can make the carriers move mainly up and down by the expandable particles. Consequently, the present invention can easily control the movement of the remote-acting bodies at low cost. Also, the present invention enables various controls by combining various kinds of remote-acting bodies.

According to a twentieth aspect of the invention, the above mentioned objects are achieved by providing an apparatus for manipulating carriers holding micro-substances, wherein the remote-manipulating means is an optical source such as a laser ray or an infra-red ray and so on when the remote-acting bodies are micro-organisms having lumino-taxis, or transparent or opaque substances.

The present invention, the apparatus can draw the carriers close near focal points having high energy density by irradiating a ray such as laser to the transparent substance and can transfer the carriers by moving the irradiation of the ray. Besides, in the present invention, the apparatus can easily control positions of the carriers by irradiation the laser and so on to the opaque substance, and giving heat to expand the volume. Furthermore, the present invention can easily execute complicated controls of the position of carriers by using micro-substances, without labor for treating.

According to a twenty-first aspect of the invention, the above mentioned objects are achieved by providing an apparatus for manipulating carriers holding micro-substances, wherein plural kinds of remote-manipulating means are mounted. The present invention can execute various and complicated controls according to the used substances or purpose, for instance, by combining magnetic field with electric field and so on.

According to a twenty-second aspect of the invention, the above mentioned objects are achieved by providing a method of controlling a position of carrier holding micro-substances comprises the steps of: pouring remote-acting bodies for. positions thereof to be manipulated by a remote force, micro-substances including target substances of an assay and so on, the carriers capable of holding micro-substances and the remote-acting bodies, into a liquid, a gas or a solid in accordance with a predetermined order, agitating the suspension to hold micro-substances and the remote-acting bodies in the carriers, controlling positions of the carriers holding micro-substances and the remote-acting bodies in the surfaces thereof by applying a remote force to the remote-acting bodies.

Here, "a predetermined order" is variously determined according to the remote-acting bodies, micro-substances or carriers to be used or the purpose of the kinds of the inspections. For example, in the first embodiment, the magnetic particles are poured into lastly, because bonding between magnetic particles and the carrier may prevent from bonding between bacteria and the carrier. Besides, "agitating" increases the opportunity of encounter among carriers, remote-acting bodies and micro-substances, and contributes to insertion of the micro-substances and so on into the holes and so on of the carriers and promotion of construction of the carriers holding micro-substances.

The present invention can easily, reliably and rapidly execute assays and so on without manpower, at low cost, because carriers holding micro-substances can be constructed in the suspension during process, and need not be treated for the constructions beforehand.

In the present invention, the carriers holding micro-substances can satisfy both superior remote-acting ability and superior capturing ability by combining the remote-acting bodies having superior remote-acting ability with the carriers having superior capturing ability, and can efficiently and rapidly execute assays and so on, with high precision in determination on the quantity.

Furthermore, in the present invention, the carriers holding micro-substances are capable of various movements, and precision and complicated controls. The present invention provides with the carrier holding micro-substances that can carry and transfer such useful substances (immune substances and so on) as medical supplies to the destinations without contamination. The present invention can effectively utilize for processing of, inspection and analyze of useful substances, extraction and analyze of gene substances (DNA and so on), and inspection of immune substances (antibodies) and so on.

According to a twenty-third aspect of the invention, the above mentioned objects are achieved by providing a method of controlling positions of carrier holding micro-substances, wherein the remote-acting bodies, micro-substances and carriers are described in the second to the twelfth aspects. The present invention can execute inspections and so on with respect to various substances, in various modes.

According to a twenty-fourth aspect of the invention, the above mentioned objects are achieved by providing a method of controlling positions of carriers holding micro-substances, comprises the steps of: pouring a sterilized reductive enzyme, such micro-organisms such as bacteria or viruses being a target substance of an assay and so on, and sterilized cellulose-carriers in a sterilized liquid culture medium, pouring magnetic particles in the liquid culture medium, agitating the liquid suspended by them, controlling positions of the micro-organisms and so on by applying or removing a magnetic field.

Here, the present invention uses the sterilized liquid culture medium, the sterilized reductive enzyme, and the sterilized magnetic particles, in order to inspect existence of micro-organisms, measure the quantity of micro-organisms, and extract DNA/RNA from micro-organisms. The reductive enzyme is used for detection of the existence of micro-organisms. For example, T.T.C. that is used as a reductive enzyme, makes insoluble coloring matter by reduction.

According to a twenty-fifth aspect of the invention, the above mentioned objects are achieved by providing a method of controlling positions of carriers holding micro-substances, comprises the steps of: pouring cellulose-carriers having a plurality of cavities or holes, magnetic particles, and micro-substances such as antibiotin or anticancer substance, agitating the liquid suspended by them, controlling positions of the carriers holding micro-substances and the remote-acting bodies in the surfaces thereof by applying or removing a magnetic field to or from the remote-acting bodies.

The present invention has in addition to the above effect, such merits that it is chemically stable, it affects no bad influence to the target substances for assay etc., it is reliable, and it is capable of being selected variously according to the target substances and so on.

Furthermore, the carrier holding micro-substances can transfer and carry the useful substances such as medical supplies (antibiotic and so on) to the destination, without contamination. The present invention can effectively utilize for easy and rapid processing of inspections and analyze of useful substances, extraction and analyze of gene substances (DNA and so on), and inspections and analyze of immune substances (antibody) and so on, and can contribute to the automatic performance of the clinical inspection and so on.

Furthermore, such substances and cells that can be adsorbed to the carriers, can be recovered and concentrated by making use of orientation in a magnetic field.

According to a twenty-sixth aspect of the invention, the above mentioned objects are achieved by providing a method of controlling positions of carriers holding micro-substances, comprises the steps of: pouring micro-substances being hard to be filtered, remote-acting bodies, and carriers into a liquid, agitating the liquid suspended by them, controlling so as to use the remote-acting bodies and carriers as auxiliary chemicals for filtration by applying or removing a magnetic field to of from the liquid.

The present invention makes a filtrating separation be more reliable, less contaminated, and less laborious than a filter. The present invention enables micro-substances that are hard to be filtrated, to be filtrated easily and surely by suspending the remote-acting bodies and carriers.

The present invention can improve the efficiency of adsorbing and filtrating by using the carrier as auxiliary chemicals for adsorbing and filtering, utilizing orientation by magnetic field, controlling the density of carriers, and avoiding clog and so on. Furthermore, the present invention can safely, automatically and easily execute multi-stage chemical reactions by transferring the carriers between containers in order,.

DESCRIPTION OF THE PREFERRED EMBODIMENTS

A first embodiment of the invention will be described below.

The first embodiment relates to an example of Rapid Minimum Inhibitory Concentration Measure.

Figure 2:
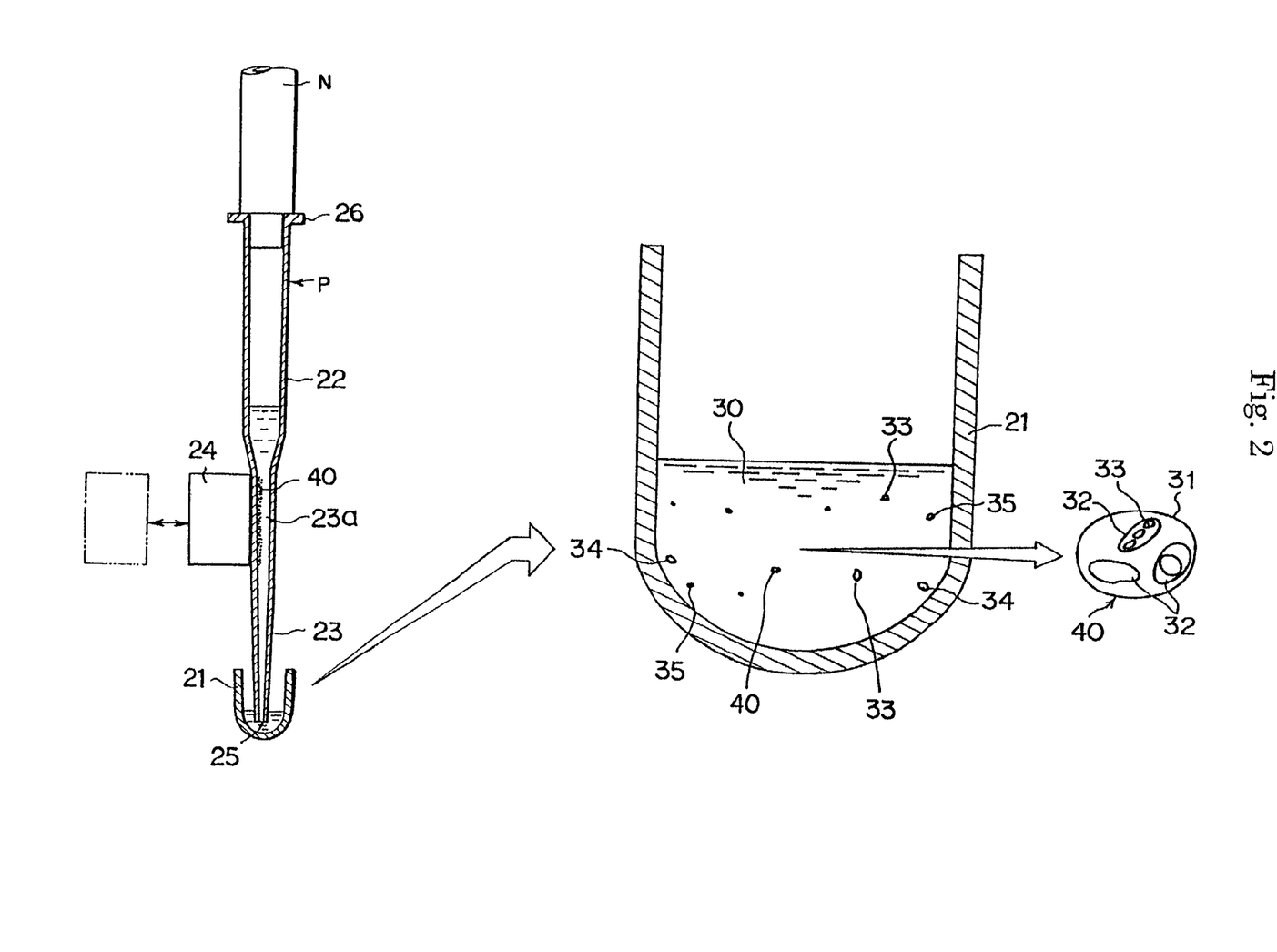
FIG. 2 is an enlarged fragmentary schematic illustration of the carrier holding micro-substances of the first embodiment of the invention.

As shown in FIG. 2, this embodiment uses a magnetic particle 33 as a kind of remote-acting bodies whose positions can be manipulated by a remote-acting magnetic field, bacteria 34 as a target substance of an assay, and a sterilized C.C. (cellulose carrier) 31 capable of holding said magnetic particles 33 and bacteria 34 in the surface thereof as the carrier.

The bacteria of more than about 100 CFU (colony forming unit)/ml are prepared, in consideration of accuracy in measuring. Those substances are separately prepared beforehand, then suspended in a liquid. A sterilized liquid culture medium 30 is prepared as a liquid for suspension, and the magnetic particles 33, bacteria 34 and C.C. 31 are poured in and suspended.

Furthermore, in this suspended liquid, sterilized T.T.C. (tetrazolium chloride, or tetrazolium bromide and so on) 35 whose quantity is 0.05% of the liquid culture medium is suspended therein. In the present embodiment, the liquid culture medium, for example, a sterilized (or bioclean) culture medium (sterile medium), for example, Müller Hinton (M.H.), nutrient, heart-infusion (H.I.), and so on, is prepared in a container.

In the present embodiment, the assay is executed by a sample distributor comprises, for example, as shown in FIG. 2, one or more well-plates 21 accommodating a liquid, a pipette tip P having a front end portion 25 tapered off toward the front end, a reservoir portion 22 with a greater diameter than the front end portion 25, a liquid passing portion 23 slightly narrower than the reservoir portion 22, and a separation region 23a in the liquid passing portion 23 subjected to an action of a magnetic field; a sample distribution unit (not shown) having a nozzle N removably fitted into an cavities of the reservoir portion 22 to apply a negative or positive pressure into the pipette tip P to draw or discharge a liquid into or from the pipette tip P; a magnet (M) 24 arranged so that it can be brought close to or away from the liquid passing portion 23; and a control device (it is not shown in drawings) for controlling the operation and movement of the sample distribution unit, the attaching and detaching of the pipette tip P to and from the nozzle N, and the bringing of the magnet 24 close to or away from the pipette tip P.

Besides, in FIG. 2, reference numeral 26 shows an edge part to have hardness to the opening of the reservoir portion 22. Said sample distribution unit is detachably mounted at the upper end of pipette tip P, is connected with pipette tip P, and is such a mechanism for drawing and discharging liquid as a cylinder. It is needless to say that the shape of the pipette tip P is not limited to the one shown in drawing. As far as the micro-substances-holding carriers 40 are surely collected by magnet 24, any shapes may be used. In order to collect by the magnet completely, it is preferable that the diameter of the section the magnet attached or detached is formed to be thinner and the speed of drawing or discharging is controlled so as to increase attracting-efficiency.

The magnetic field generated by the magnet 24 is strong enough to attract and maintain C.C. 31 holding the magnetic substances 33 and bacteria 34 on the wall of the liquid passing portion 23 of the pipette tip P, and does not affect C.C. 31 holding magnetic particles 33 in the case that the magnet 24 is farthest away from the pipette tip P. Further, in FIG. 2, micro-substances-holding-carriers 40 and so on in the well-plate 21 is enlarged for convenience's sake.

Next, the processing of the present embodiment is described.

Figure 3:
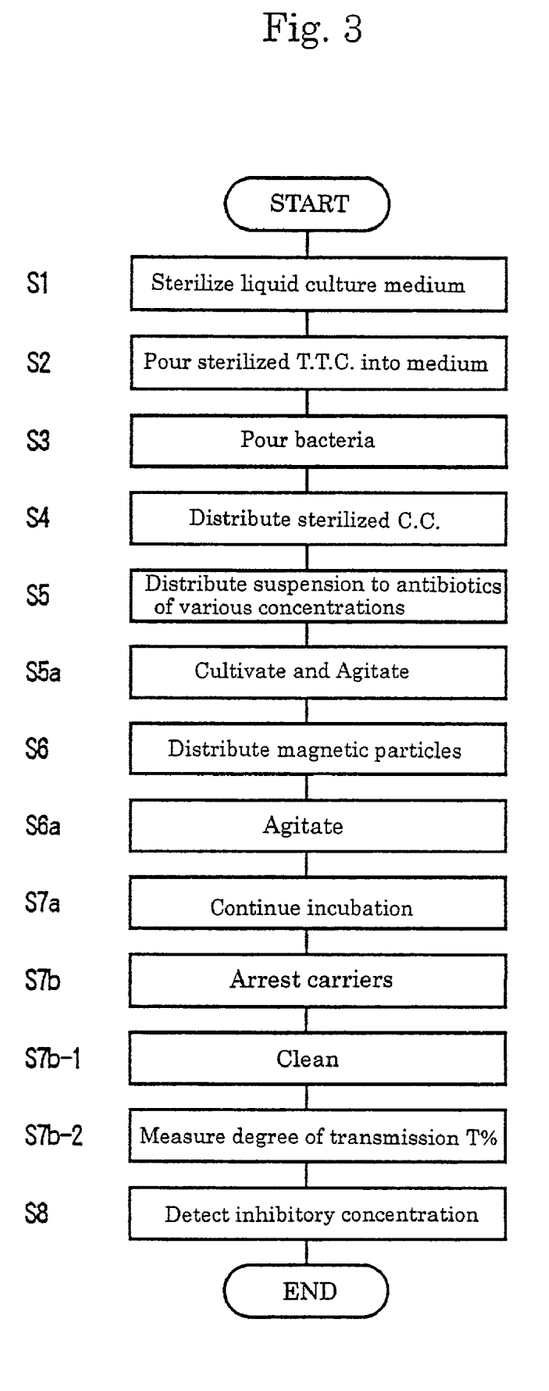
FIG. 3 is a flowchart of the first embodiment of the invention.

In FIG. 3, at step S1, the liquid culture medium, for example, the sterilized culture medium (Sterile Medium), for example, Müller Hinton (M.H.), nutrient and so on is accommodated in the well-plate 21. Sterilization is performed by an autoclave for about twenty minutes at temperature of 120° C.

At step S2, said T.T.C. 35 which is the reduced substance sterilized by Milipore-filter is poured into the liquid culture medium 30, as a marker substance, so as to be 0.05% (ratio of capacity).

The T.T.C. 35 sticks on bacteria. If the bacteria stuck by T.T.C. 35 take oxygen in, Formazan which is an insoluble red coloring matter is generated by reductive power of bacteria. Therefore, the quantity of bacteria can be detected by measuring that of the red coloring matter. Thus, as T.T.C. 35 is apt to turn red by heat, T.T.C. 35 is sterilized by Milipore filter without heat.

At step S3, the bacteria (or micro-organisms including viruses and so on) of 100 CFU (Colony Forming Unit)/ml of bacteria 34 are poured into the liquid culture medium 30. This quantity of bacteria is determined so as to be necessary for keeping measuring accuracy above a fixed level.

At step S4, furthermore, said cellulose carriers (C.C.) sterilized by using ethylene oxide gas, are distributed by the pipette tip P. Here, said cellulose carrier (C.C.) 31 has a sphere whose diameter is about 150 μm and has a plurality of holes 32 whose diameter is about 10 μm, in the sphere. The hole is large enough for the magnetic particles held therein so as to be able to cause the orientation by the magnetic field from the magnet 24. Also, the cellulose carrier 31 has a charge of 1.16 meq./g. Namely, in the present embodiment, the carriers are capable of holding micro-substances and so on by both fixing in holes 32 and Coulomb force of the charge. Also, for example, the number of the C.C. 31 is determined to be 100 sphere/ml, so that the bacteria of 1 CFU can be held in each C.C. 31.

At step S5, a plural solutions of antibiotics used as samples, whose concentration is each 200, 100, 50, 25, 12, 5, 3, 0 γ/ml, is prepared in different containers (micro-plate). The suspended liquid obtained at step S4 is distributed into each container by the pipette tip P.

At step S5a, the suspended liquid accommodated in each container is cultivated at temperature of 37° C. for 6–8 hours. This cultivation is executed in order to increase the number of the bacteria up to being enough to measure. If the sufficient quantity of bacteria is prepared beforehand, this step is not necessary. The cultivation is executed in the state that Milipore filter that passes Oxygen but does not pass vapor, is put on the container, in order to prevent from invading various kinds of germs.

At this stage, a mixer is driven to rotate and agitate bacteria 34 for two minutes. The agitation may be executed by applying super-sonic wave or repeating to draw and discharge by the pipette device. In this case, agitation of the distributed suspension, namely the culture medium 30 is performed at angular velocity of 200–300 rpm and amplitude of 2 mm.

At step S6, the magnetic particles 33 are distributed by the pipette tip P. Here, DYNA Beads: M-450/CD3 (a brand name) ($4 \times 10^8$ beads/ml) is used. About this particles of $10^5$/ml are poured into. In this case, magnetic particles of $10^3$/sphere are contained per a carrier. As the diameter of the magnetic particles is about 500 Å–1000 Å and the size of holes of C.C. is about 10 μm, the quantity of magnetic particles is large enough to make the magnetic particles execute orientation and receive the influence of magnetic field.

At this stage, a mixer is driven for two minutes in order to blend the bacteria 34. The agitation may be executed by applying super-sonic wave. In the case of the mixer, the culture medium 30 that is a suspended liquid distributed, is agitated by oscillation of angular velocity of 200–300 rpm and amplitude of 2 mm, for two minutes. The magnetic particles are distributed after that the bacteria 34 are poured into at step S6. Because, the magnetic particles are apt to stick to carriers, and bacteria 34 can be desired to be held in carriers as much as possible. Further, because the magnetic particles should not much influence bacteria and the magnetic particles are only used for collecting bacteria.

By the agitation, the carriers, C.C. 31 encounter magnetic particles 33 and bacteria 34 which are target substances, and the carrier holding micro-substances are constructed by fixing or absorbing.

At step S7*a*, the incubation is continued. Before long, the liquid culture medium 30 that is a suspended liquid, becomes more red.

At step S7*b*, the magnetic field is applied to the separation region 23*a* in the liquid passing portion 23 by bringing the magnet 24 close to the liquid passing portion 23 of the pipette tip P. In order to attract the C.C. 31 holding the magnetic particles 33 and bacteria 34 by the magnet 24, three times of pumping are executed so as to pass the liquid through separation region 23*a*.

At step S7*b*-1, extracting the coloring matter and cleaning are executed by acetone of 80%. In this case, the coloring matter which is insoluble to water can be extracted by dissolving in acetone and three times of pumping, while the magnet 24 is close to the liquid passing portion 23. Besides, when the T.T.C. that is soluble in water, is used, the coloring matter can be extracted not by acetone, but by cleaning.

At step S7*b*-2, the degree of transmission T % is measured by irradiating the ray with 550 nm wavelength into the extracted liquid.

At step S8, the increase in the quantity of bacteria is detected for each concentration of antibiotics. The minimum concentration at which the increase in the quantity of the bacteria is not observed, is the threshold of concentration which can inhibit the increase of the bacteria. The quantity of bacteria at the early state, can be measured by detecting the threshold. Conversely, this method can specify a kind, a concentration, and an antibacterial effect of antibiotics that are effective for bacteria.

The other example of the embodiment is described. In this example, instead of said T.T.C. of marker substance, fluorescence is adhered to the bacteria. The minimum concentration for inhibiting the increase in the quantity of bacteria may be detected by direct measurement of number of the bacteria. This measurement is performed by observing the excited light whose wavelength is different from a predetermined wavelength of incidence irradiated to the bacteria adhered by fluorescence. In this case, measurement can be performed rapidly.

Furthermore, chemical luminescent substances used as a marker substance may be adhered to the captured bacteria, instead of fluorescence. In this case, chemical luminescence (acridinium) can be measured without irradiating light, by using aqueous solution of hydrogen peroxide.

The micro-substances are not limited to the bacteria or viruses, and the marker substances are not always necessary, in the above-mentioned examples. Further, the suspended systems are not always limited to the above-mentioned liquid. Also, each quantity and number is not limited to the above-described case. The carrier is not limited to the above-mentioned C.C.

The present embodiment can easily and rapidly execute the automatic performance of inspection for effective concentration of antibiotics, as easy and rapid inspection is possible by adhering and holding the bio-active-substances (antibiotics and so on) and assay-test-micro-organisms (assay-test-micro-organisms for antibiotics: colon bacilli and so on) and cultivating.

Next, the second embodiment is described.

Figure 4:
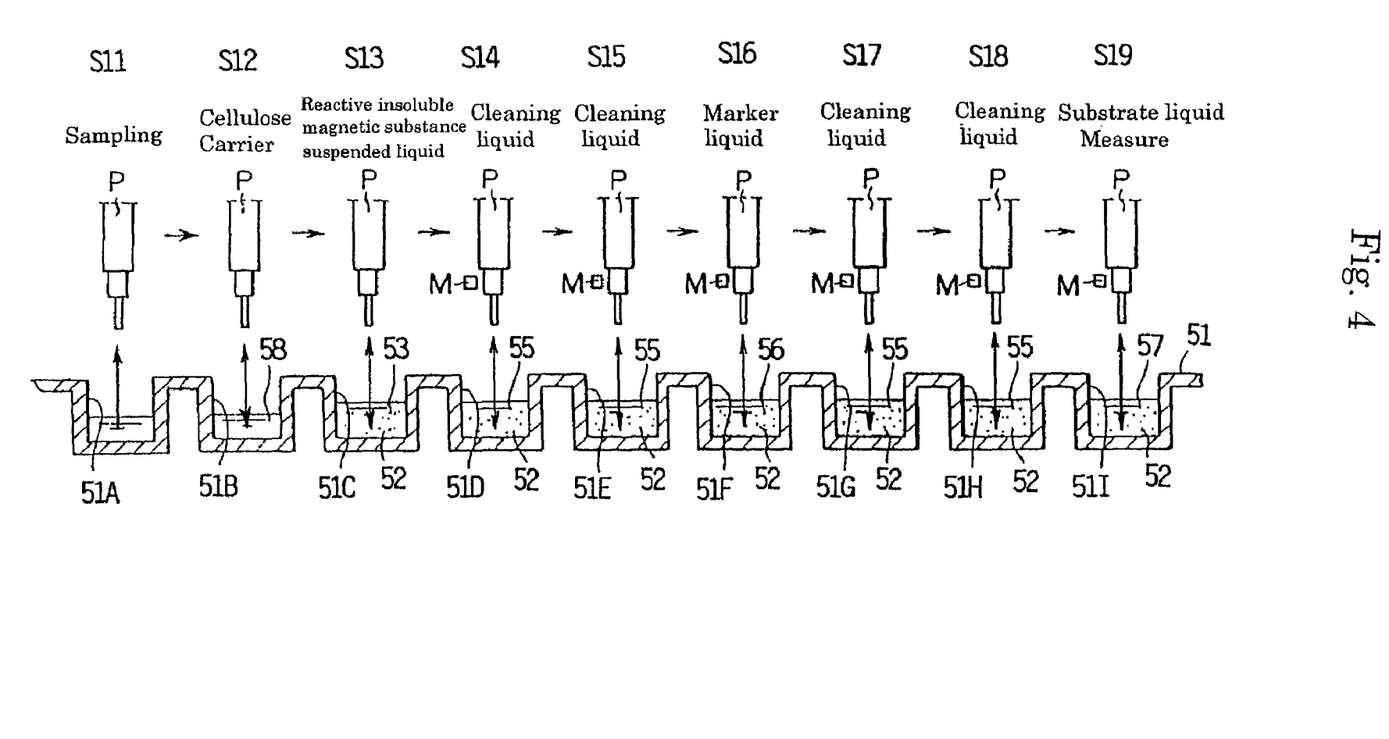
FIG. 4 is a flowchart of the second embodiment of the invention.

The present embodiment shows the case of extracting DNA or/and RNA from bacteria, for example. The present embodiment comprises steps S1–S6 except step S5 for cultivating bacteria and so on, step S6 for distributing and agitating the magnetic particles, and step S7*b* for capturing the carriers, in such a manner as the first embodiment.

The steps of the present embodiment thereafter are different from the first embodiment. At the step S7*b*-1 of the present embodiment, the protein bonded to DNA is denatured by SDS or proteinase K so as to facilitate to resolve. Thereafter, DNA is dissolved and extracted by three times pumping and cleaning in the phenol solution. After adding EtBr (Ethidium Bromide), the extracted DNA is irradiated by ultra-violet ray, and DNA or RNA can be detected by receiving fluorescence. Also, DNA can be detected by observing fluorescence by Fluoro-Flow method. Furthermore, chemiluminescence method can be used. DNA can be detected or extracted by using a single strand of DNA as probe, whose base sequence is known, hybridizing complementarily, and forming a double helix.

The third embodiment is described below.

The third embodiment uses a carrier which is formed to be a ball made of cellulose (for example, cellulose acetate) having about 150 μm diameter. The ball having a plurality of cavities or holes of about 10 μm in the surface thereof is used. Also, the magnetic particles having about 1 μm diameter are used as a remote-acting body. The C.C. of about 1000/ml and the magnetic particles are suspended in a liquid that includes kanamycin of about 1 g/ml used as micro-substances. Thereafter, a suspended liquid is generated by agitation with mixer or applying super-sonic wave. This suspended liquid is drawn into the pipette as mentioned above. On the occasion of drawing the liquid, the magnetic field is applied by the magnet used as a magnetic source, brought close to the liquid passing portion.

The cellulose spheres holding magnetic particles are attracted and settled. The supernatant liquid is abandoned, and then a physiological salt solution is poured in, to generate the suspended liquid again.

At the next step, said suspended liquid including cellulose spheres holding magnetic particles and kanamycin is injected to a vein of a tail of mouse. Then the magnetic particles held in carriers can be attracted, transferred, and collected to the root part of the tail by approaching a magnet thereto.

As transfer and orientation of the carrier holding the specified substances and magnetic particles can be performed in human beings and animals, this method can be used for collecting the medicine at the point of disease in order to treat such disease as infection and so on, and can avoid the secondary effect (an effect at different places from the point) (Drug Delivery System; DDS). Also, a cancer can effectively be treated by transferring and collecting the carriers holding antitumor-agent (such as Cis-Platin and so on) with a magnet.

The fourth embodiment is explained on the basis of flow chart of FIG. 4. The present embodiment shows an example that the carrier holding the magnetic particles, micro-substances including a target substance of the assay etc. is applied to the immunoassay. Said sample distributor of FIG. 2, and, pipette or disposable pipette tip attached to the distributor, are used for the control of this embodiment.

In this case, as shown in FIG. 4, the container is formed to be cassette-like. The container has plural vessels, in which samples or reagents necessary for reaction or processing are distributed beforehand. The liquid passing portion having the separation region of the pipette tip P attached to a nozzle of liquid suction line having at least one nozzle, is formed so as to be capable of transferring the carriers holding magnetic particles maintained on the inner wall thereof. The cassette-like container may have one row of the vessels or micro-plate-like plural rows. In the case of micro-plate, the liquid suction line can be arranged so as to be multi-channel, corresponding to the vessels.

In FIG. 4, reference mark P shows the pipette tip which distributes a predetermined quantity of a sample which is a target substance, from a parent container accommodating a blood sample and so on (not shown in drawings) to an ample reaction container 51, and draws or discharges insoluble magnetic particles suspended liquid 53, a cleaning liquid 55, a marker liquid 56, a substrate liquid 57, a cellulose carriers (C.C.) suspended liquid 58 and so on, Here, the carrier holding magnetic particles means the carrier holding magnetic particles, micro-substances including a target substance of the assay etc. in the surface thereof.

Also, the sample reaction container 51 has plural vessels 51A–51I arranged to be column-like, in a series, loop-like, or zigzag-like. In vessel 51A, the sample is roughly distributed beforehand. In vessel 51B, the cellulose-carriers suspended liquid 58 is accommodated beforehand. In vessel 51C, a predetermined quantity of the insoluble magnetic particles suspended liquid 53 is accommodated beforehand. In vessels 51D and 51E, a predetermined quantity of the cleaning liquid 55 is accommodated beforehand. In vessel 51F, a predetermined quantity of the marker liquid 56 is accommodated beforehand. In vessels 51G and 51h, a predetermined quantity of the cleaning liquid 55 is accommodated beforehand. Furthermore, in vessel 51I, the substrate liquid 57 is distributed, and the vessel 51I is constructed so as to be able to measure the luminescence.

Further, in the case of assay of CLIA and CLEIA, the sample reaction container 51 is made of opaque materials that do not give the influence of luminescence one another. In the case of assay of EIA, at least the bottom of the container 51 is made of transparent material.

When the immunoassy is executed by using said sample reaction containers 51 and the pipette tip P, at step S11, the predetermined quantity of the sample which is distributed to vessel 51A roughly, is drawn into the pipette tip P to quantitatize.

At step S 12, the pipette tip P which draws this sample is transferred in order to discharge the entire quantity of the sample drawn into the vessel 51B accommodating the C.C. suspended liquid 58. Thereafter, the mixture of the sample liquid and the C.C. suspended liquid is repeatedly drawn and discharged and the entire or predetermined quantity of suspended liquid is drawn into the pipette tip P.

At step S13, the entire suspended liquid drawn in the pipette tip P is transferred and discharged into the vessel 51C accommodating the magnetic particles suspended liquid 53. Thereafter, the mixture of the sample, the C.C. and the insoluble magnetic particles are repeatedly drawn and discharged to generate the uniformly agitated mixture of the sample, C.C. and the magnetic particles.

Thus, samples and magnetic substance 53 are held in the surface of the C.C.. After elapse of time required, the entire or predetermined quantity of the incubated mixture incubated are drawn in the pipette tip P. Then, the carriers 52 holding the magnetic substances and samples suspended in the mixture are attracted on the inner wall of the liquid passing portion 23 by the magnetic force of the magnet 24 fitted outside of the pipette tip P. Also, a lower level of the drawn liquid is controlled to be near or higher than the lowest part of the magnet 24, in order to be capable of arresting whole the carriers holding the magnetic substances.

Here, the strength of the magnetic field of the magnet should fall within the range that the carriers holding magnetic substances can be attracted and maintained and can be released by two or three times of repeats of drawing and discharging. The strength of the magnetic field is determined by the position of the magnet, diameter of the liquid passing portion 23, a kind of the suspension liquid, and, size, mass, and materials and so on of the carrier and so on. Thus, after that the carriers 52 holding magnetic substances 53 are collected again, the mixture excluding the carriers 52 holding magnetic substances, is discharged into the vessel 51C to be eliminated, and only the carrier holding magnetic substances remains in the pipette tip P. Then, as the carriers holding magnetic substances are wet, the carriers are arrested and maintained on the inner wall of the liquid after the mixture is discharged. Therefore, even if the pipette tip P is transferred, the carriers do not fall off easily.

Next, at step S14, the pipette tip P is transferred to the next vessel 51D together with the carriers 52 being collected, and draws the cleaning liquid 55 in the vessel 51D. In this case, the magnet 24 is moved away from the pipette tip P, and carriers 52 are released from the arrested state.

Then the carriers 52 holding magnetic substances can effectively be cleaned by drawing and discharging the cleaning liquid 55. After completion of drawing and discharging the liquid 55, the entire cleaning liquid 55 in vessel 51D is slowly drawn into the pipette tip P. Then the magnet 24 is brought close to the pipette tip P again, and collects whole the carriers holding magnetic substances 53 suspended in the drawn cleaning liquid 5. The cleaning liquid 55 excluding the carriers 52 holding magnetic substances are discharged into vessel 51D and eliminated, and only carriers 52 remain in said pipette tip P.

At step S15, said pipette tip P is transferred to the next vessel 51E together with the collected carriers 52. Then, the cleaning liquid 55 in vessel 51E is drawn, and the cleaning work and collecting work are executed in such a manner that executed in vessel 51D.

At step S16, said pipette tip P attracted by carrier 52 is transferred to the next vessel 51F. The marker liquid 56 in the vessel 51F is drawn into the pipette tip P.

Then the magnet 24 is brought away from the pipette tip P, and releases the carriers 52 holding magnetic substances from the arrested state. Consequently, reaction between the carriers 52 holding magnetic substances and the marker liquid 56 can be executed uniformly.

Then, at step S17, after completing to drawing and discharging, the liquid is incubated for a required time. Thereafter, the entire marker liquid 56 in vessel 51F is slowly drawn. Then, the magnet 24 is brought close to the pipette tip P again, and whole the carriers suspended in the drawn marker liquid 56 are arrested. The marker liquid 56 except the carriers 52 are discharged into vessel 51F and is eliminated, and only the carriers remain in the pipette tip P.

Thereafter, at step S18, the above pipette tip P in which the carriers holding magnetic substances are collected, is transferred to the next vessel 51G. The cleaning liquid in vessel 51G is drawn into the pipette tip P. After cleaning and collecting carriers 52 holding magnetic substances in such a manner that is executed in vessel 51D, 51E, the cleaning liquid 55 in vessel 51H is drawn, in such a manner that is executed in vessel 51G, and the carriers 52 holding magnetic substances are cleaned and collected.

Thereafter, at step S 19, the pipette tip P is transferred to the vessel 51I. In the case of a method such as assay of CLEIA, that continues luminescence after mixing with the substrate liquid and needs a fixed time for stabilizing the quantity of luminescence. The pipette tip P draws the substrate liquid 57 accommodated beforehand in vessel 51I. Then, the magnet 24 moves apart from the pipette tip P, and the carriers 52 holding magnetic substances are released from the collected state. Therefore, reaction between whole the carriers 52 holding magnetic substances and the substrate liquid 57 can be uniformly executed by drawing and discharging the substrate liquid 57.

Then, after completion of drawing and discharging and incubation for a required time, the quantity of luminescence is measured by an optical measuring unit.

The present embodiment can apply to the other method of assay.

For example, the present embodiment can apply to EIA method and so on.

Also, the present embodiment can apply to such a method of assay or an apparatus for clinical inspection that uses immune substances, biological substances or molecular substances such as antigen, antibody, protein, enzyme, DNA, vector-DNA, m-RNA or plasmid, or, marker substance necessary for determining the quantity or property such as isotope, enzyme, chemiluminescence, fluo-luminescence, electro-chemical-luminescence.

Furthermore, for example, the present embodiment can apply to immunoassay, inspection for chemical reaction, or, the unit for extraction, recovery, or isolation of DNA and so on.

The present embodiment can safely (without cross-contamination) and easily execute multi-stage chemical reactions by transferring between reaction containers one by one.

The fifth embodiment is described below.

The present embodiment is the one which uses the carriers holding the dielectric bodies used as remote-acting bodies, having dielectricity being higher or lower than that of liquid, micro-substances or the carriers, instead of magnetic particles.

For example, it is well known that there is alumina, silicon gum, or acetone etc. as substances having high specific dielectricity. Further, there is ferro-electricity. Electric field generated between electrodes mounted outside of the container, are applied to the substances, in order to manipulate the carriers remotely by using dielectric substances or charged substances,.

Usually, in the case of supplying big voltage between electrodes, alternating high-frequency wave of electric field can be applied in order to avoid the generation of reaction between electrodes (electrolysis). Thus, the carrier holding the dielectric substances and micro-substances can be moved by using the interaction between the alternating electric field and electro-dipole induced in the objection,.

In this case, if one of electrodes is formed to be sharp, carriers holding micro-substance can be transferred toward this electrode, because the electric field of electrode formed to be sharp is stronger than the other electrode. Also, if the polarity of voltage supplied to the electrodes reverses, the direction of polarization induced in carriers holding micro-substances is revered. Therefore, the direction of power on the carriers does not vary by the reversing, and the electro-phoresis is possible. The polarity induced is changed according to whether the dielectricity of dielectric substances used as a remote-acting body is lower or higher. In the case of the lower dielectricity, as the power directing the carriers to the electrode having weak electric field is stronger than the other electrode, the carriers can move in reverse direction to the above case. The size of holes of the carrier is large enough to perform the orientation of the magnetic particles.

In the case of utilizing electric field in the suspended liquid, the electric conductivity of the solution should be lower to a certain extent, to avoid excess Joule's heat. Furthermore, the present embodiment is capable of controlling plural pairs of electrodes as well as a pair of electrodes, synchronously so as to execute the complicated movement such as rotation.

The sixth embodiment is described below.

The present embodiment is the one that carriers hold both charged substances and magnetic substances used as remote-acting bodies. The present embodiment can control complicated movement such as transferring, rotation, or stationary by applying electric field and/or magnetic field.

Oscillating or rotating the remote-acting bodies by applying or oscillating the magnetic field by solenoid used as a remote-manipulating means, or by movement of charged substances such as synchrotron movement, can remove the remote-acting bodies from the carriers, make the remote-acting bodies hold in the carriers, or agitate the carriers.

The seventh embodiment is described below.

The present embodiment can trap the remote-acting bodies such as high molecular micro-particles suspended in liquid so as to be sandwiched between two opposite rays of laser. Furthermore, the present embodiment can generate a change of the momentum of light between before and after the incidence by irradiation to the transparent bodies, remote-acting bodies, having refractive index different from the surrounding medium.

The change of the momentum is given to the micro particles according to the law of conservation of momentum. As a result, radiation pressure is generated. In the case when the refractive index of the micro-particles is higher than surrounding medium, these total powers face the direction of the focal points of laser, and restrain Brownian motion, and can trap the micro-particles in the position balanced with the external force such as gravity.

The trapped micro-particles follow the movement of the focal points of the laser. Thus, the present embodiment can execute observation and so on with respect to a single micro-particle, by trapping the micro-particles at the focal points of the optical unit. Furthermore, various movements are possible by making the carriers hold magnetic particles and so on.

The eighth embodiment is described below.

As the present embodiment, it is explained that the substance having a higher expansion coefficient than the surrounding suspended liquid is used in the carrier. When the substance is used, the carriers can rise by raising temperature, and can fall by lowering temperature. Such substance is for example, body having a gas wrapped by elastic film. Also, the same control is possible by irradiating the light such as laser and so on to the opaque substances.

Besides, in the above-mentioned description, only the case when the carrier is C.C. is shown. But, the present invention is not limited to the case. Furthermore, as the magnetic source, the electromagnetic or superconducting electromagnet as well as magnet can be used. Furthermore, the carrier can hold two or more kinds of substances used as remote-acting bodies and be controlled by two or more remote-acting means.

The invention claimed is:

1. A method of controlling a position of carriers holding micro-substances comprises the steps of:
    pouring remote-acting bodies which can be positionally manipulated by a remote force, micro-substances including a target substance of an assay, and carriers having surfaces with a plurality of holes, cavities, concavities or convexities that are sized to be capable of holding the micro-substances and the remote-acting bodies, into a liquid in accordance with a predetermined order,
    making the remote-acting bodies and the micro-substances be held in the holes, cavities, concavities or convexities in the surfaces of the carriers by agitating the remote-acting bodies, the micro-substances, the carriers, and the liquid, and
    controlling positions of the carriers holding the micro-substances and the remote-acting bodies in the surfaces thereof by applying a remote force to the remote-acting bodies,
    the pouring comprising pouring sterilized reductive enzyme into the liquid in addition to the remote-acting bodies, the micro-substances, and the carriers, and
    comprising selecting the carriers to be sterilized cellulose-carriers, selecting the liquid to be a sterilized liquid culture medium, selecting the remote-acting bodies to be magnetic particles, and selecting the remote force to be a magnetic field.

2. A method of controlling positions of carriers holding micro-substances according to claim 1, further comprising controlling the magnetic field so as to control the positions of the carriers in a manner which causes filtering of the micro-substances through separation from the liquid or gas of the carriers with the remote-acting bodies and micro-substances held thereto.

3. A method of controlling positions of carriers holding micro-substances according to claim 1 comprising, prior to the pouring, separately preparing the carriers, the remote-acting bodies, and the micro-substances.

4. A method of controlling positions of carriers holding micro-substances according to claim 1, comprising selecting the micro-substances to comprise one of bacteria and viruses.

5. A method of controlling positions of carriers holding micro-substances according to claim 1, comprising selecting the predetermined order to be addition to the liquid culture medium in sequence the sterilized reductive enzyme, the micro-organisms, the sterilized cellulose-carriers, and the magnetic particles.

6. A method of controlling positions of carriers holding micro-substances according to claim 1, comprising selecting the micro-substances to comprise one of antibiotics and anticancer substances.

7. A method of controlling positions of carriers holding micro-substances according to claim 1, wherein the agitating includes using a mechanical force.

8. A method of controlling a position of carriers holding micro-substances comprises the steps of:
    pouring remote-acting bodies which can be positionally manipulated by a remote force, micro-substances including a target substance of an assay, and carriers having surfaces with a plurality of holes, cavities, concavities or convexities that are sized to be capable of holding the micro-substances and the remote-acting bodies, into a liquid or a gas in accordance with a predetermined order,
    making the remote-acting bodies and the micro-substances be independently held in the holes, cavities, concavities or convexities in the surfaces of the carriers by simultaneously agitating the remote-acting bodies, the micro-substances, the carriers and the liquid or gas,
    controlling positions of the carriers holding the micro-substances and the remote-acting bodies in the surfaces thereof by applying a remote force to the remote-acting bodies,
    selecting the carriers to be cellulose-carriers having therein the plurality of cavities, concavities, convexities or holes,
    selecting the remote-acting bodies to be magnetic particles,
    selecting the remote force to be a magnetic field,
    controlling the magnetic field so as to control the positions of the carriers in a manner which causes filtering of the micro-substances through separation from the liciuid or gas of the carriers with the remote-acting bodies and micro-substances held thereto,
    carrying out the agitating in a manner that includes using a mechanical force; and
    configuring the carriers so that the holes, cavities, concavities or convexities are large enough to allow the magnetic particles to undergo orientation therein in response to the magnetic field.

* * * * *

UNITED STATES PATENT AND TRADEMARK OFFICE
CERTIFICATE OF CORRECTION

PATENT NO. : 7,071,006 B2  Page 1 of 1
APPLICATION NO. : 10/042373
DATED : July 4, 2006
INVENTOR(S) : Hideji Tajima and Yoshiro Okami It is certified that error appears in the above-identified patent and that said Letters Patent is hereby corrected as shown below:

On Title Page, Item (62)

Under "Related U.S. Application Data"

Please change "Sep. 9, 1997" to --June 9, 1997--

Column, 22, line 50, change "liciuid" to --liquid--

Signed and Sealed this

Third Day of April, 2007

JON W. DUDAS
*Director of the United States Patent and Trademark Office*